United States Patent [19]

Silvian

[11] Patent Number: 4,947,407
[45] Date of Patent: Aug. 7, 1990

[54] SAMPLE-AND-HOLD DIGITAL PHASE-LOCKED LOOP FOR ASK SIGNALS

[75] Inventor: Sergiu Silvian, La Crescenta, Calif.

[73] Assignee: Siemens-Pacesetter, Inc., Sylmar, Calif.

[21] Appl. No.: 391,215

[22] Filed: Aug. 8, 1989

[51] Int. Cl.$^5$ ............................................. H03D 1/00
[52] U.S. Cl. .................................. 375/94; 329/347; 128/419 R
[58] Field of Search ...................... 375/39, 41, 42, 94, 375/96, 75; 329/304, 317, 347; 340/825.77; 128/419 R, 419 P, 419 PG

[56] References Cited

U.S. PATENT DOCUMENTS

| | | | |
|---|---|---|---|
| 4,215,430 | 7/1980 | Johnson, Jr. | 375/111 |
| 4,509,171 | 4/1985 | Brenier | 375/42 |
| 4,571,550 | 2/1986 | Head | 375/39 |
| 4,575,682 | 3/1986 | Aoyagi et al. | 375/39 |
| 4,580,276 | 4/1986 | Andruzzi, Jr. et al. | 375/42 |
| 4,675,619 | 6/1987 | Uchibori et al. | 375/41 |
| 4,788,696 | 11/1988 | Sakane et al. | 375/42 |
| 4,805,189 | 2/1989 | Mahony | 375/96 |

OTHER PUBLICATIONS

Holmes, J. K. et al., "A Second Order All-Digital Phase-Locked Loop," *IEEE Transactions on Communications* (Jan. 1974), pp. 62–68.

"Types SN54LS297, SN74LS297 Digital Phase-Locked Loop Filters," *Texas Instruments Digital IC Handbook*, (Jan. 1981), pp. 38–42.

*Primary Examiner*—Douglas W. Olms
*Assistant Examiner*—Stephen Chin
*Attorney, Agent, or Firm*—Bryant R. Gold; Leslie S. Miller; Lisa P. Weinberg

[57] ABSTRACT

A digital phase-locked looped generates a clock signal synchronized with a carrier signal modulated by amplitude shift keying (ASK). During periods when no carrier signal is present, the generated clock signal coasts at the frequency of the carrier signal most recently present, rather than trying to phase-lock on noise. A binary controlled digital oscillator generates the clock signal. A phase detector determines the difference between the phase of the carrier signal, when present, and the local clock signal. When the average amplitude of the carrier signal exceeds a prescribed threshold level, the phase detector output is sampled and passed to an integrator circuit, where the phase difference is integrated. The output of the integrator circuit is applied to a pulse generator, causing the pulse generator's duty cycle to change proportionally. In turn, the pulses are applied to the binary controlled digital oscillator, causing the frequency of the local clock signal to shift in a direction that minimizes the phase error between the local clock signal and the carrier signal. When the average amplitude of the carrier signal is less than the prescribed threshold level, the phase detector output is not smapled. In such case, the output of the integrator circuit remains at the value obtained from the most recent prior phase detector sample.

26 Claims, 4 Drawing Sheets

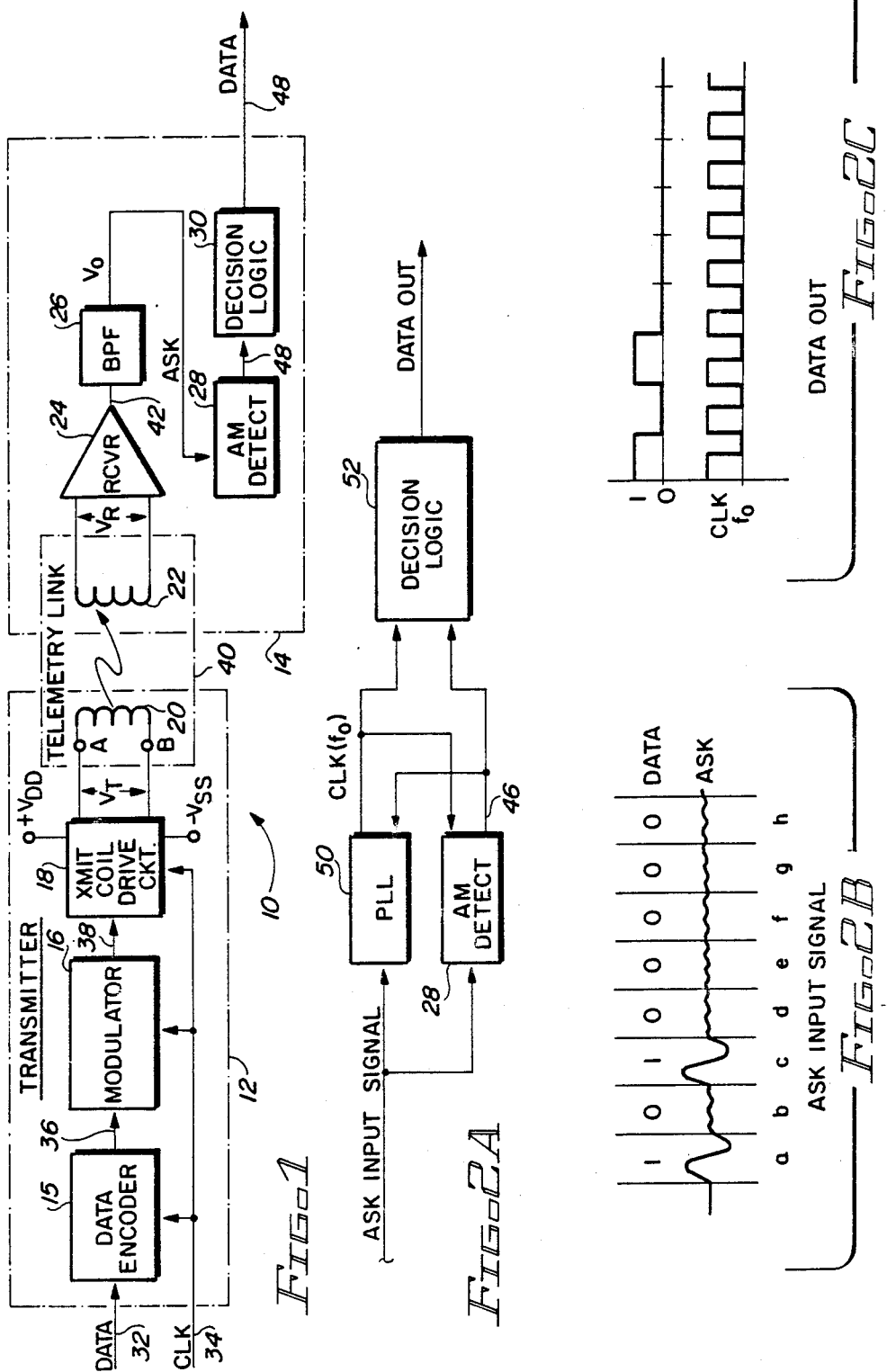

SAMPLE-AND-HOLD DIGITAL PHASE-LOCKED LOOP FOR ASK SIGNALS

BACKGROUND OF THE INVENTION

The present invention relates to demodulation circuits, and more particularly to a digital phase-locked loop circuit that generates a local clock signal that is phase-locked to a carrier signal modulated by amplitude shift keying (ASK). Once such a phase-locked clock signal is generated, it can be efficiently used to accurately demodulate the ASK signal.

Modern communication channels utilize a variety of modulation schemes for passing information on a carrier signal from one location to another. One common modulation scheme, for example, is amplitude modulation (AM). An AM signal is one wherein the amplitude of the carrier signal changes as a function of the information to be transferred. Where the information to be transferred is presented in binary form—having one of two possible values—an AM carrier signal thus assumes one of two amplitudes depending upon the particular binary information that is to be transmitted. Hence, where the binary information may be described as being a "1" or a "0", an AM carrier signal modulated with such binary information assumes a first peak amplitude corresponding to the transfer of a "1", and a second peak amplitude corresponding to the transfer of a "0".

One particular form of binary AM modulation involves making one of the two amplitudes of the carrier signal a known value, and making the other of the two amplitudes zero. In such a case, the transfer of a "1", for example, is indicated by the presence of the carrier signal, and the transfer of a "0" is indicated by the absence of the carrier signal. (These roles could, of course, be reversed, with a "1" being indicated by the absence of the carrier signal, and a "0" being indicated by the presence of the carrier signal.) Such a modulation scheme is a simple form of amplitude shift keying (ASK), wherein the amplitude of the carrier signal shifts between one value and zero. That is, the carrier signal is keyed on and off, as the binary information transferred shifts between one value and another.

ASK has long been a preferred type of modulation for many applications because of its simplicity. More recently, in the implanted device telemetry art, the use of duobinary modulation has been proposed in order to allow a high bit rate to be transferred efficiently (at a low signal-to-noise ratio) through the limited bandwidth channel existing between an implantable device and a non-implantable device, such as between an implantable pacemaker and its corresponding external (non-implanted) programmer. See Applicant's copending patent application, Ser. No. 07/391,080, filed 08/08/89, entitled "High Speed Digital Telemetry System Implantable Device." As indicated in that patent application, the reception of a duobinary encoded signal results in an ASK signal that must be demodulated in order to extract the digital data information therefrom. Advantageously, such ASK signals may be asynchronously demodulated using very simple inexpensive passive demodulation circuits, e.g., comprising a diode, a resistor and a capacitor. Unfortunately, while simplicity and low cost are highly desired characteristics for a demodulation circuit used with implantable devices, such asynchronous demodulation is generally not suitable for use in the high bit rate implantable device art because of the low bit error rates that such implantable device art demands. Hence, there is a need in the implantable device art for a simple synchronous demodulation scheme that can easily, accurately, and inexpensively demodulate ASK signals at low bit error rates. (The "bit error rate" is a measure of how many errors occur as digital information is passed from one location to another. A low bit error rate indicates few errors occur, and is preferred for reliable transmission.)

It is well known in the telemetry art that the bit AM error rate can be dramatically improved using a synchronous demodulation scheme. In a synchronous demodulation scheme, a local, noise free, clock signal is generated that is "phase-locked" to the received carrier signal. By "phase-locked" it is meant that the frequency of the local clock signal is the same as, or integrally related to, the frequency of the carrier signal; and that the phase of the clock signal, typically measured at the data transitions, maintains a fixed known relationship relative to the phase of the carrier signal, typically measured at the zero crossings of the carrier signal. With a noise free clock signal phase-locked to the carrier signal, a synchronous demodulator can easily be used, as per known art. Usually, it is a multiplier having the received signal at the analog input and the regenerated clock at its digital input.

A phase-locked clock signal is typically generated using a phase-locked loop (PLL). A PLL generally includes a voltage controlled oscillator (VCO) that generates a local clock signal having a frequency proportional to a control voltage. The phase error between the clock signal and the carrier signal is measured in a phase detector circuit. The resulting phase error signal is then used as the control voltage to change the frequency of the VCO by an amount that minimizes the phase error between the two signals, thereby phase-locking the clock signal to the carrier signal. (Note that an instantaneous change in the frequency of the clock signal changes its phase.)

One of the problems associated with ASK signals, and the main problem that leads to unacceptably high bit error rates, even when synchronous detection is used, is that the ASK signal may include long sequences when no carrier signal is present. That is, if a digital "1" is represented, for example, by the presence of the carrier signal and a digital "0" is represented by the absence of the carrier signal, and if the digital word "0100000" is transferred using ASK modulation, ⅞ of the transferred word is represented by no carrier signal. During this time, a PLL or equivalent circuit is seeking a carrier signal to lock to when in fact no such signal is present. Hence, during such times when the carrier signal is absent, the locally generated clock signal locks on noise, causing the clock signal to jitter and to assume an erroneous phase relationship relative to the bit times of the data, thereby resulting in an incorrect decision as to the value of a given bit.

To overcome the problem created by long sequences of no carrier signal, the prior art teaches using a modulation scheme that avoids such sequences. For example, frequency shift keying (FSK) and/or phase shift keying (PSK) both include a transition in the carrier signal regardless of whether a "1" or a "0" is being represented. Hence, the carrier signal is always present, and the PLL always has a data transition on which a clock signal can be phase locked. Unfortunately, however, for some applications, e.g., the implantable device art, FSK or PSK modulation may not be preferred because, e.g., the available bandwidth of the communications channel does not allow an efficient transfer of data using these types of modulation. For other applications, while FSK or PSK modulation may be preferred for the transmission channel, processing of the received data when encoded using a duobinary encoding scheme nonetheless results in an ASK signal that must still be demodulated, as indicated in applicant's referenced patent application, "High Speed Digital Telemetry System for Implantable Device." Thus, for such applications where ASK signals are used, or otherwise result from the processing of the transferred signal, what is needed is a synchronous demodulation system that is not adversely affected by a long sequence (e.g., several sequential bits) of the absence of the carrier signal.

Another solution to the problem of long sequences of no carrier signal in an ASK signal is to use a bit encoding scheme that does not permit more than one or two bits of the same value to be transmitted sequentially. Such encoding schemes are well documented in the art and are commonly used in more sophisticated communication channels in order to measurably improve the bit error rate. However, such improvement is achieved only at the expense of more complex encoding and decoding systems. For the implantable device art, where simplicity and low cost are major factors influencing the type of circuits that are used, such complex and sophisticated bit encoding schemes are generally not practical. What is needed, therefore, is a simple and reliable synchronous demodulation system that is not dependent upon a particular encoding scheme that limits the number of consecutive 1's or 0's that may occur in the transmitted data.

SUMMARY OF THE INVENTION

The present invention provides a simple second order, sample-and-hold digital phase-locked loop that addresses the above and other needs. In accordance with the present invention, a clock signal is provided that is synchronized with an ASK modulated carrier signal for so long as the ASK carrier signal is present. When the ASK carrier signal is not present, e.g., during long sequences of all 0's, the generated clock signal coasts at the frequency of the carrier signal that most recently occurred, rather than trying to phase-lock on noise.

The sample-and-hold digital phase-looked loop of the present invention includes: (1) a binary controlled digital oscillator that generates a local clock signal; (2) a pulse generator that controls the binary controlled digital oscillator; (3) a phase detector circuit that measures the phase difference or error between the local clock signal and the carrier signal; (4) a sampling circuit that samples the measured phase difference at least once during each cycle of the local clock signal if the amplitude of the carrier signal exceeds a prescribed threshold; and (5) an integrator circuit that integrates the sampled phase error, applying the resulting integrated output to the pulse generator in order to control its pulse width. If no sampled phase error is presented at the input of the integrator, e.g., when the amplitude of the carrier signal does not exceed the prescribed threshold, then the integrator maintains (holds) its output at the level determined from the most recent sampled phase error appearing at its input.

In operation, the phase detector determines the difference between the phase of the carrier signal and the local clock signal. When the amplitude of the carrier signal exceeds a prescribed threshold level, as determined by examining the amplitude of an AM demodulation signal of the carrier signal, the phase detector output is sampled and passed to an integrator circuit, where the phase difference is integrated. The output of the integrator circuit is then applied to the pulse generator, causing the pulse generator's pulse width (duty cycle) to change, which pulse width change causes the phase of the local clock signal to shift in a direction that minimizes the phase error between the local clock signal and the carrier signal. When the amplitude of the carrier signal is less than the prescribed threshold level, the phase detector output is not sampled, but its output is discharged to ground. In such case, the output of the integrator circuit remains at the value obtained from the most recent prior phase detector sample.

In the preferred embodiment, the output of the integrator circuit, which output represents a sampled value of the phase error, functions as a control signal that is applied to the pulse generator. The pulse generator thus produces a pulse width having a duty cycle proportional to the sampled phase error. When the duty cycle is greater than 50%, the local clock signal shifts its phase in one direction; when the duty cycle is less than 50%, the local clock signal shifts its phase in the other direction. When the duty cycle is equal to 50%, the local clock signal maintains its present phase. The integrator, pulse generator, digital oscillator and other parts, as will be explained, form a second order analog/digital PLL. Known digital PLLs are generally first order. See, e.g., Holmes, J. K., "A Second Order All-Digital Phase-Locked Loop," IEEE Trans. Communications, January 1974, pp. 62–68. However, known second order PLL's are too complex and costly to be practical for many simpler applications, such as the implantable device field. Hence, a simpler second order PLL is needed.

The present invention is ideally suited for use in a communication channel established between an implantable device and a non-implantable device wherein an ASK data signal is received in one of the implantable or non-implantable devices. In such a communication channel, a first binary state is signaled within the ASK data signal by the presence of a carrier signal, and a second binary state is signaled within the ASK data signal by the absence of the carrier signal. It thus becomes necessary to demodulate the ASK data signal using the demodulation apparatus of the present invention. This demodulation apparatus, in accordance with one embodiment of the invention, includes: (1) means for generating a clock signal that is phase-locked with the carrier signal of the ASK data signal when the carrier signal is present within the ASK signal, and that is phase-locked to the carrier signal that was most recently present within the ASK data signal when the carrier signal is absent from the ASK data signal; and (2) decision means synchronized with the clock signal for: (a) determining whether the received ASK data signal indicates a first binary state, and if so for how many periods of the clock signal the first binary state continues; and (b) determining whether the received ASK data signal indicates a second binary sate, and, if so, for how many periods of the clock signal the second binary state continues. Advantageously, with such apparatus, i.e., with a clock signal that is phase-locked to the carrier signal, a data stream of binary bits encoded within the ASK data signal (where each binary bit comprises a prescribed number of periods of the carrier signal during which the ASK data signal assumes either the first or second binary state) can be readily and accurately extracted.

Another embodiment of the present invention may be described as including apparatus for generating a clock signal that is phase-locked with an amplitude modulated (AM) carrier signal. In accordance with this embodiment, the apparatus includes: (1) means for generating a local clock signal that has a frequency approximately equal to the frequency of the carrier signal, the frequency of the local clock signal being adjustable as controlled by a control signal; (2) phase detector means for detecting the phase error between the carrier signal and the local clock signal; (3) sampling means for sampling the phase error detected by the phase detector means at least once during each period of the carrier signal if the average amplitude of the AM carrier signal exceeds a prescribed value, and for not sampling the phase error if the average amplitude of the AM carrier signal is less than the prescribed value; (4) integrating means for integrating (summing) the most recent sampled phase error obtained from the sampling means and for holding the resulting integrated sampled phase error until the sampling means again samples the phase error between the input signal and the clock signal, an output signal of the integrating means thereby comprising the integral of the last recent sampled phase errors presented to the input of the integrating means; and (5) means responsive to the output signal of the integrating means for generating the control signal, the control signal being applied to the local clock signal generating means in order to adjust the frequency thereof in a direction that minimizes the phase error between the local clock signal and the AM carrier signal. Apparatus as thus described advantageously causes the local clock signal to assume a frequency that is phase-locked to the AM carrier signal when the average amplitude of the AM carrier signal exceeds the prescribed level, and to assume a frequency that is the same as the most recent AM carrier signal that had a average amplitude exceeding the prescribed level when the peak amplitude is less than the prescribed level.

The invention may also be considered as including a method for extracting a clock signal that is phase-locked with an ASK input signal. Such a method includes the steps of: (a) generating a local clock signal having a frequency that varies as a function of a control signal; (b) detecting the phase difference between the ASK input signal and the local clock signal; (c) generating an error signal as a function of the phase difference detected; (d) sampling the error signal only when the amplitude of the ASK input signal exceeds a prescribed threshold value; (e) integrating the sampled error signal; (f) generating the control signal as a function of the integrated sampled error signal obtained in the previous step and maintaining the value of the control signal at a substantially constant value until the error signal is again sampled; and (g) adjusting the frequency of the local clock signal as a function of the value of the control signal.

It is one aspect of the present invention to provide a sample-and-hold digital phase-locked loop (PLL) circuit wherein the phase error between an input signal and a clock signal (the PLL's output signal) is sampled only when the average amplitude of the input signal exceeds a prescribed threshold level.

It is another aspect of the invention to provide such a digital PLL wherein the sampled value of the phase error is held until the next sample is taken at a time when the average value of the carrier signal exceeds the threshold, thereby assuring that the clock signal of the PLL does not attempt to lock on low level input signals, but rather coasts at the right frequency until a new phase error sample is available.

Yet another aspect of the invention is to provide a digital PLL as described above wherein the frequency, and thereby the phase, of the clock signal can be adjusted to any value within a range of $f_0 \pm f_0/k$ (where $f_0$ is the center frequency of the clock signal, and $k$ is a selectable parameter), not just to discrete values within such range, as is common in prior art digital PLL's.

A still further aspect of the invention is to provide a PLL including the features and aspects described above that is inexpensive to fabricate, simple to operate, and yet provides accurate performance.

BRIEF DESCRIPTION OF THE DRAWINGS

The above and other aspects, features and advantages of the present invention will be more apparent from the following more particular description thereof, presented in conjunction with the following drawings wherein:

FIG. 1 is a block diagram of a high bit rate telemetry system;

FIG. 2A is a block diagram illustrating the manner in which ASK data may be demodulated using the present invention; FIGS. 2B and 2C are waveforms of input and output signal;

DETAILED DESCRIPTION OF THE INVENTION

Figure 3A:
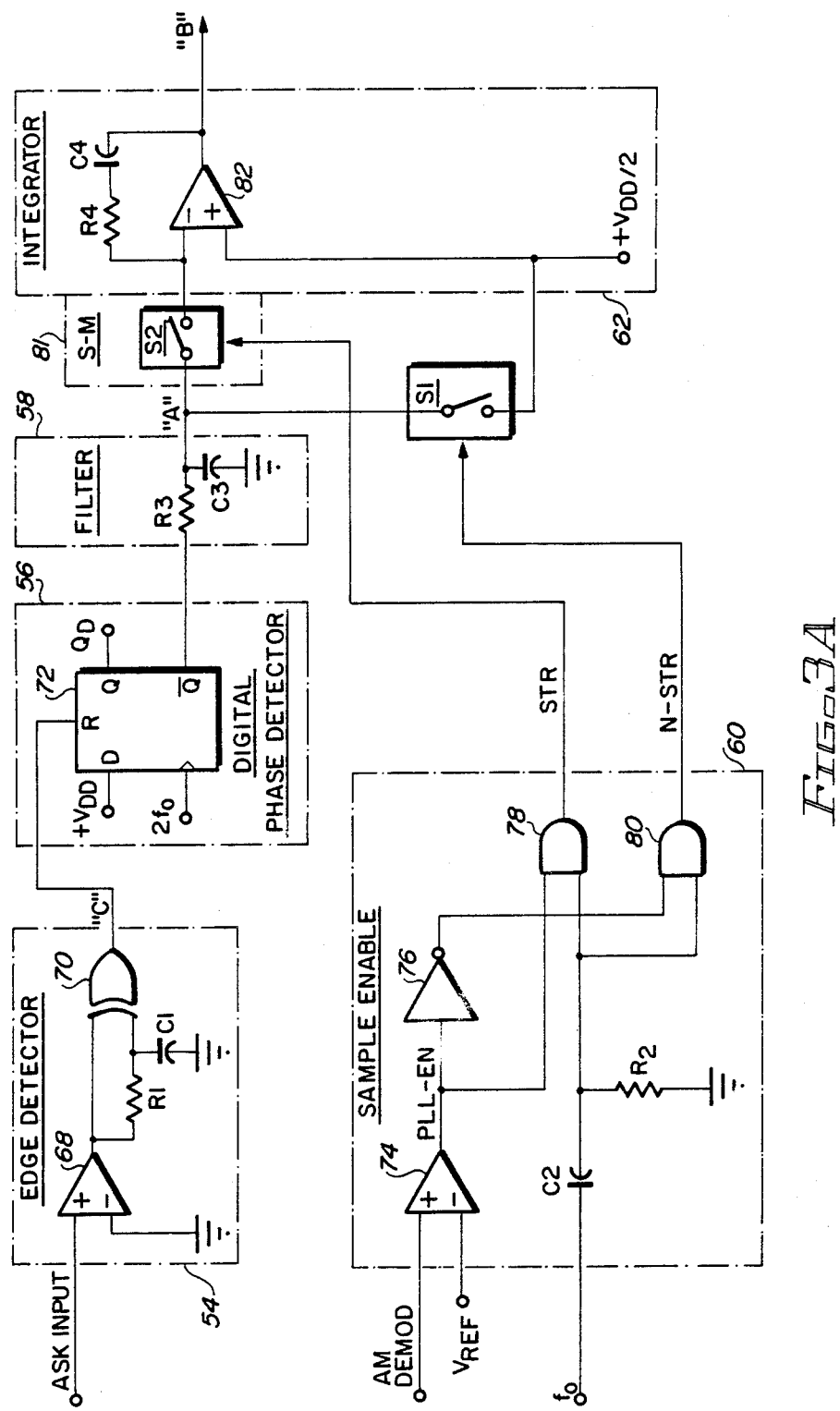
FIGS. 3A and 3B are schematic block diagrams (one being the continuation of the other) of the sample-and-hold digital ,phase-locked loop apparatus of the present invention.

The following description is of the best mode presently contemplated for carrying out the invention. This description is not to be taken in a limiting sense, but is made merely for the purpose of describing the general principles of the invention. The scope of the invention should be ascertained with reference to the claims.

In the description of the invention that follows, like numerals or reference designators will be used to refer to like parts or elements throughout.

FIG. 1 shows a simplified block diagram of telemetry system 10, and will be described first to present an overview of the type of communications channel with which the present invention may best be used. The telemetry system 10 includes a transmitter 12 and a receiver 14. The transmitter 12 includes a data encoder 14, a modulator 16, a transmit coil drive circuit 18, and a transmit coil 20. The receiver includes a receive coil 22, a receiver amplifier 24, a bandpass filter (BPF) 26, an AM detector 28, and decision logic 30. While the present invention is directed primarily to apparatus and methods for performing the function of the AM detector 28 and of the decision logic 30, it will nonetheless be helpful in understanding the present invention to also have an appreciation for the functions performed by the other elements in the communications channel with which the present invention must interface. In a preferred embodiment, the transmitter 12 is included as part of an implantable device, and the receiver 14 is included as part of an external device. However, it is to be understood that these roles could be reversed, with the receiver being included in the implantable device and the transmitter being included in the external device. In a typical application, both a transmitter and a receiver are included as part of an implantable device, and both a transmitter and a receiver are included as part of an external device.

The transmitter 12 receives as input signals a data signal, identified as DATA in FIG. 1, over an input signal line 32, and a clock signal, identified as CLK, over an input signal line 34. (Hereinafter, the signals appearing on these signal lines, as well as other signals appearing on other signal lines, may be referred to by the reference numeral of the signal line on which the signal appears, e.g., "the DATA signal 32," or "the clock signal 34.") As will be explained more fully below, the DATA signal 32 comprises a stream of binary data bits, typically in an NRZ (non-return-to zero) format (although other suitable binary formats could likewise be used) flowing at a given bit rate, $B_0$. An NRZ signal comprises a signal having two levels, with a first level representing a binary bit "1", and a second level representing a binary bit "0". If the bit rate $B_0$, for example, is 8000 bits per second (8 kbps), then one bit flows into the data encoder 14 over the data line 32 every 0.125 milliseconds (1/8000=0.000125).

The clock signal 34 used at the transmitter typically includes a plurality of synchronized clock signals derived from a common clock signal source. These clock signals are shown in the block diagram of FIG. 1 as a single clock signal 34 for simplicity of presentation. At least one of these clock signals has a frequency equal to the bit rate $B_0$.

In operation, the input data stream 32 is encoded in the data encoder 14, resulting in an encoded data stream that is presented to the modulator 16 over signal line 36. As set forth in applicant's copending patent application, referenced above, a preferred encoding scheme provides efficient bandwidth compression, meaning that the encoded data 36 can be transferred to the receiver through a channel having a narrower bandwidth than would otherwise be possible. An encoding scheme that allows such a bandwidth compression is a correlative encoding scheme, commonly referred to as duobinary encoding.

The modulator 16 modulates an appropriate carrier signal with the encoded data 36. The resulting modulated carrier signal is applied to the transmit coil drive circuit 18 over signal line 38. The carrier signal has a frequency $f_0$, and is derived from the clock signal 34. It is preferred that the carrier signal have the same frequency as the input data stream. That is, $B_0 = f_0$. While numerous forms of modulation could be used, a PSK modulation is preferred. In PSK modulation, the phase of the carrier signal is reversed 180 degrees for each change in the modulating signal. Thus, for the system shown in FIG. 1, and assuming a PSK modulation of the carrier, the modulated carrier signal 38 includes a phase reversal of the carrier signal for each data transition, or other encoding mark, found in the encoded data 36.

The transmit coil drive circuit 18 applies the modulated carrier signal 38 to the transmit coil 20. This signal is then inductively coupled, or otherwise transferred, to the receive coil 22. The coupling between the transmit coil 20 and the receive coil 22 thus forms a telemetry link 40 between the implanted coil (either the transmit coil 20 or the receive coil 22) and the external coil (the other coil).

The voltage received at the receive coil 22, $V_R$, is amplified in the receiver amplifier 24 and presented to a bandpass filter 26 over signal line 42. The bandpass filter 26 has a bandwidth BW centered about the frequency $f_0$, the frequency of the carrier signal. Any frequencies outside of the passband are not passed through the filter 26. This is particularly advantageous for rejecting EMI caused by low frequency line frequencies, such as a 60 Hz power signal. Those portions of the amplified received signal 42 that are close to the carrier signal frequency $f_0$ are readily passed through the bandpass filter 26. However, because the amplified received signal 42 includes a phase reversal of the carrier signal for each mark in the encoded data 36, and because such phase reversal represents an instantaneous frequency shift to roughly $2f_0$, significant portions of the amplified received signal 42 will not pass through the bandpass filter 26. The result is that the output signal of the bandpass filter, $V_0$, appears as an ON-OFF keyed signal, with some portions being ON and having a frequency of substantially $f_0$, and other portions being OFF (no signal present). Thus, the output from the bandpass filter is an ASK signal, wherein the pattern of the ON-OFF keying of the signal $V_0$ tracks the pattern of the input DATA signal 32. Hence, by demodulating the signal $V_0$ in an appropriate manner, this data can be recovered.

FIG. shows the bandpassed signal $V_0$ being applied to an AM detector circuit 28. The AM detector circuit detects the envelope or average amplitude of the bandpassed signal $V_0$. This amplitude substantially tracks the informational content of the input DATA signal 32. The output of the AM detector circuit 28 is presented to appropriate decision logic 30 over signal line 46. The decision logic makes a decision as to whether the ASK signal at any given instant in time is representative of a binary "1" or a binary "0". Once this decision is made, a DATA output signal can be created and presented on signal line 48.

A simple AM detector circuit includes a diode, a resistor and a capacitor. Such a simple circuit, or equivalents thereof, when coupled to a appropriate decision logic circuit, allows the data to be readily recovered.

As indicated previously, however, in order to improve the bit error rate to acceptable levels, it is preferred that a synchronous detector be used. The present invention advantageously describes a relatively simple and inexpensive circuit that accomplishes this synchronous detection function.

Referring to FIG. 2A, a block diagram of a synchronous detection circuit in accordance with the present invention is shown. The detection circuit includes the AM detector 28 of FIG. 1, as well as a phase-looked loop (PLL) circuit 50 and a decision logic circuit 52. The ASK input signal (e.g., obtained from the output of the bandpass filter 26 in FIG. 1) is applied to the PLL circuit 50 and the AM detection circuit 28. This ASK signal includes a carrier signal during those times when one bit value is to be represented, and does not include a carrier signal during those times when another bit value is to be represented. For example, as shown in the waveform diagram illustrated in the bracketed portion of FIG. 2B (relating to the ASK input signal), an eight bit data word "1010000"may be represented in ASK as the presence of the carrier signal during first and third bit times, labeled "a" and "c", and the absence of a carrier signal during the remaining bit times, labeled "b", "d", "e", "f", "g", and "h". The carrier signal shown in the waveform bracketed portion of FIG. 2B has one complete period or cycle for each bit period. This is only exemplary, as the carrier signal could have multiple cycles or periods in each bit period.

The AM detection circuit 28, as indicated above in connection with FIG. 1, generates an envelope signal, referred to hereafter as the AM demodulated signal, that substantially tracks the amplitude of the ASK input signal. The amplitude of the ASK input signal may be measured as an average value, an RMS vale, or a peak value. The AM demodulated signal is, in effect, a signal that measures the energy content of the ASK signal. During those portions of the ASK signal when the carrier signal is present, the AM demodulated signal, i.e., the output 46 of the AM detection circuit, is at a maximum value. During those portions of the ASK signal when the carrier signal is not present, the AM demodulation signal is substantially zero.

The PLL 50 generates a clock signal at a frequency $f_0$ that is phase-locked to the zero crossings of the carrier signal within the ASK input signal during those portions of the ASK signal when the carrier signal is present, i.e., bit times "a" and "c". During those portions of the ASK signal when the carrier signal is not present, i.e., bit times "b" and "d–h", the clock signal coasts at the frequency and phase it had assumed during the most recent bit time when the carrier signal was present. In accordance with the teachings of the present invention, the presence or absence of the carrier signal is determined by examining the AM demodulation signal. When the AM demodulation signal is above a prescribed threshold, that is interpreted as conclusive evidence that the carrier signal is present. If so, the phase lock function of the PLL 50 is carried out. On the other hand, when the AM demodulation signal is below a prescribed threshold, that is interpreted as conclusive evidence that the carrier signal is not present. If so, the phase lock function of the PLL 50 is disabled, and its clock signal continues to be generated at its prior frequency and phase.

The decision logic circuit 52 receives at least the AM demodulation signal 46 and the clock signal $f_0$ as input signals and processes these signals in an appropriate manner to determine whether a "1" or a "0" is indicated. While many processing schemes may be used to achieve this function, some of which may involve the use of additional input signals, such as the ASK signal and additional clock signals, e.g., a clock signal at $2f_0$ and/or $4f_0$, the simplest processing scheme is to just sample the AM demodulated signal at the conclusion of each period of the clock signal $f_0$. This simple processing scheme can be achieved, for example, by connecting the AM demodulated signal 46 to a comparator noninverting input, the inverting input of which is tied to $V_{Ref} = V_p/2$. The output of this comparator would be connected to the data input of a D-type flip flop, and by connecting the clock $f_0$ to the clock input of the flip flop. If the AM demodulated signal is high, indicative of the presence of a carrier signal in the ASK signal, the flip flop is clocked to a "1". If the AM demodulated signal is low, indicative of the absence of a carrier signal in the ASK signal, the flip flop is clocked to a "0". In this manner, the output of the demodulation circuit assumes a binary sequence that recreates the input binary sequence, as illustrated in the output waveform diagram shown in the bracketed portion of FIG. 2C.

Figure 3B:
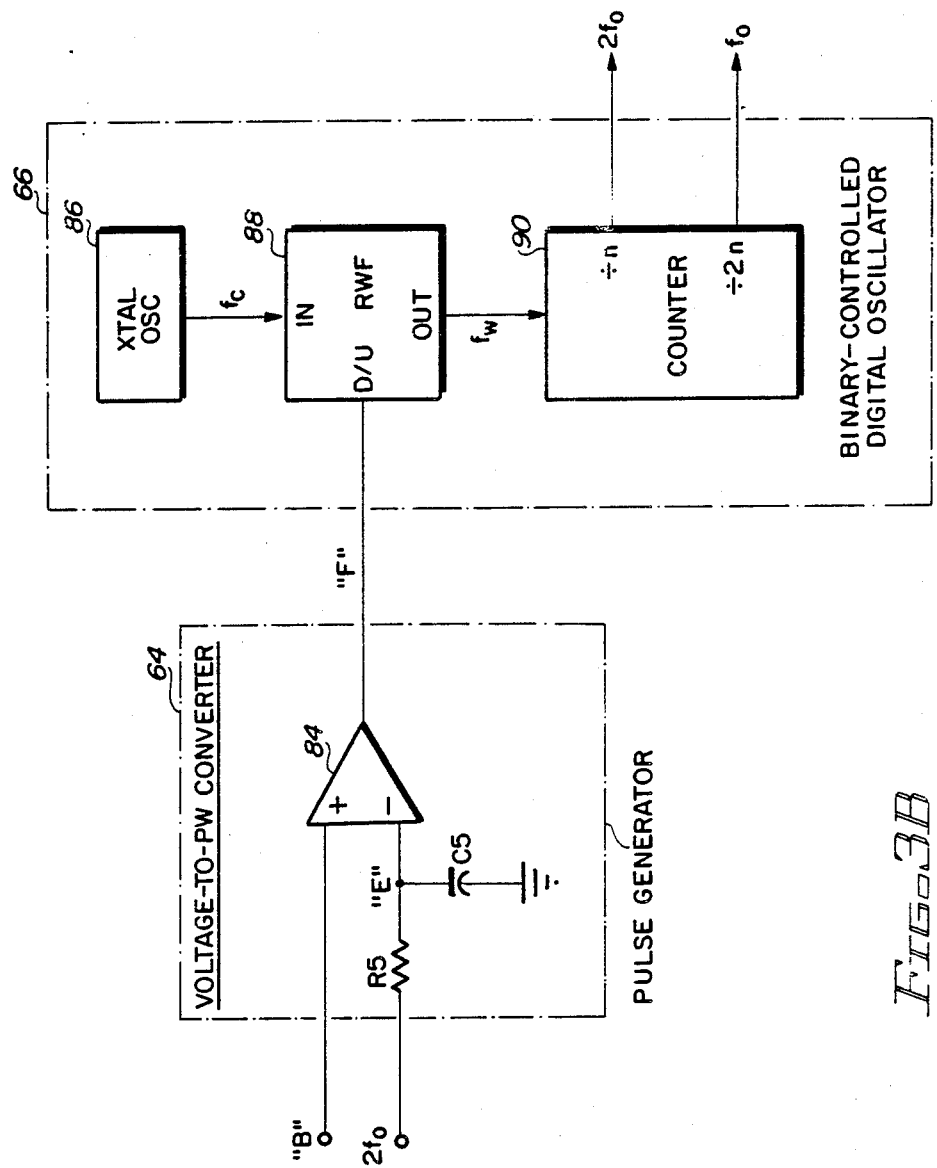
Figure 4:
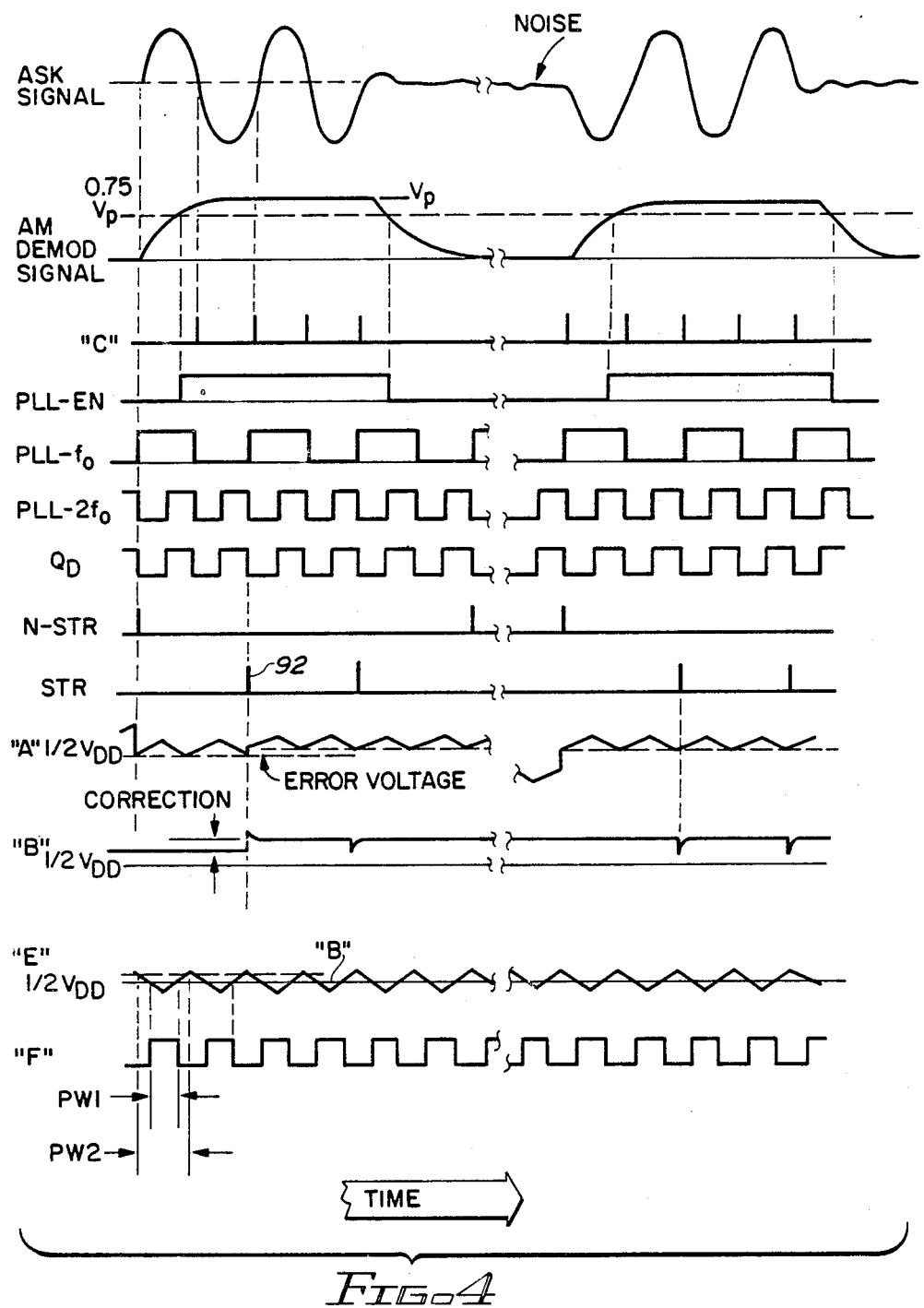
FIG. 4 is a timing waveform diagram depicting various key signals associated with the operation of the apparatus of FIGS. 3A and 3B.

FIGS. 3A and 3B are a schematic block diagram of a preferred PLL circuit 50 in accordance with the present invention. FIG. 4 is a timing waveform diagram illustrating the waveforms developed during operation of the PLL circuit 50. In the description of the PLL circuit 50 that follows, reference will be made to these figures jointly.

As seen in FIGS. 3A and 3B, the PLL circuit 50 includes an edge detector circuit 54, a digital phase detector 56, a filter 58, a sample enable circuit 60, a sample-and-hold switch S1 and a reset switch S2, an integrator 62, a voltage-to-pulse width (PW) converter 64, and a binary controlled digital oscillator 66. The edge detector circuit 54 functions as a zero-crossing detection circuit to determine the zero crossings of the ASK input signal. To this end, it includes a conventional comparator amplifier 68 having positive and negative input terminals. The ASK input signal is connected to the positive input terminal. A zero voltage reference signal, i.e., ground, is connected to the negative input terminal. Thus, the output of the comparator amplifier 68 is a pulsed wave that changes states with each zero crossing of the ASK input signal. If the ASK input signal includes a symmetrical carrier signal at a fixed frequency, the output of the comparator amplifier 68 is a square wave at that same fixed frequency. This pulsed wave output is applied to one input of a dual input exclusive OR gate 70. The other input is connected to delay filter made up of a resistor R1 and a capacitor C1, which delay filter has as its input the pulsed wave output signal from the comparator amplifier 68. Thus, in operation, changes in level of the pulsed wave signal appearing at the delay filter terminal of the exclusive OR gate 70 lag behind similar changes in level of the pulsed wave signal appearing at the other terminal of the exclusive OR gate 70. As an exclusive OR gate provides a high output signal only when there is a difference in level between its two input signals, the output signal of the exclusive OR gate, labeled "C" in FIG. 3A and FIG. 5, comprises a train of narrow pulses, with each pulse occurring coincident with the zero crossings of the ASK input signal.

The digital phase detector 56 is realized using a D-type flip flop 72. Such a flip flop changes state coincident with the positive going edge (from a low level to a high level) of a clock signal as steered by the value of the data signal appearing at its data input terminal, labeled D. If the data signal is high at the time of the positive-going clock transition, the flip flop switches to a "1" state (Q output=high level; inverse Q output=low level). If the data signal is low at the time of the positive-going clock transition, the flip flop switches to a "0" state (Q output=low level; inverse Q output=high level). Further, at any time the flip flop may be reset (set to its "0" state) by applying a reset signal to its reset terminal, R.

As shown in FIG. 3A, the flip flop 72 has a constant high level, $V_{DD}$, applied to its data input D, and the output of the zero crossing detector 54 is applied to its reset terminal R. The flip flop is clocked with a clock signal, $2f_0$, having a frequency twice that of the main clock signal, $f_0$, and synchronized with the clock signal $f_0$. Hence, in operation, the flip flop 72 is reset to its "0" state coincident with each detected zero crossing of the ASK signal, and clocked to its "1" state coincident with each positive-going edge of the $2f_0$ clock signal (which occurs twice during each cycle or period of the $f_0$ clock signal. If the zero crossings of the ASK input signal occur at the same time as the negative-going transitions of the $2f_0$ clock signal, then the flip flop 72 toggles between its two states with a 50% duty cycle, as shown by the phase detector output signal $Q_D$ in FIG. 4. If however, the zero crossings of the ASK signal do not occur at the same time as the transitions of the $2f_0$ clock signal, then the duty cycle of the phase detector output signal, $Q_D$ (or its inverse), assumes a value other than 50%.

The output of the phase detector 56 is applied to the filter circuit 58, comprising a resistor R3 and a capacitor C3. The values of R3 and C3 are selected so that the filter acts as an integrator relative to the clock periods of interest, integrating the inverse output of the flip flop 72. Thus, the output of the filter 58, identified as signal "A" in FIGS. 3A and 4, comprises a triangular waveform, which triangular waveform represents the integral of the phase detector output 56. This signal thus ramps first in one direction and then the other direction for respective time periods determined by the relative phase relationship between the ASK input signal and $2f_0$ clock signal. If the output of the phase detector is a square wave having a 50% duty cycle, i.e., if the phase error between the ASK input signal and $2f_0$ clock is zero, this triangular waveform will always ramp up and ramp down to the same values. If there is a phase error between the ASK input signal and the $2f_0$ clock signal, however, the triangular waveform will ramp up or ramp down to different values, owing to the different ramp times caused by the phase error, thereby causing an offset in the peak values of the ramped voltages to accumulate. It is noted that during these ramp times, an electrical charge is being added to (positive ramp) or removed from (negative ramp) the capacitor C3. Thus, the electrical charge on the capacitor C3 at any fixed point in time during the $2f_0$ clock cycle, provides a relative measure of the phase error detected by the phase detector 56 during that cycle.

At the end of each period of the clock signal $f_0$, the phase error charge accumulated on the capacitor C3 is either passed to the integrator circuit 62 or dumped to ground depending upon whether the carrier signal is present within the ASK input signal or is not present. The presence of the carrier signal is detected, and appropriate strobe signals are generated to effectuate the charge transfer, by the sample enable circuit 60. The sample enable circuit 60 includes a comparator amplifier 74 that compares the AM demodulated voltage signal to a reference voltage $V_{Ref}$. If the AM demodulated voltage is greater than the reference voltage $V_{Ref}$, then the output of the comparator amplifier 74, labeled PLL-EN (PLL enable) in FIGS. 3A and 4, goes high. If, on the other hand, the AM demodulated voltage is less than the reference voltage $V_{Ref}$, then the output of the comparator amplifier 74 goes low.

The output of the comparator amplifier 74 is applied to one input of a dual input AND gate 78. The inverse of the output of the comparator amplifier 74, obtained from invertor gate 76, is applied to one input of another dual input AND gate 80. Thus, AND gate 78 is enabled, and AND gate 80 is disabled, when the AM demodulated signal exceeds the threshold $V_{Ref}$. Similarly, AND gate 78 is disabled, and AND gate 80 is enabled, when the AM demodulated signal is less than the threshold $V_{Ref}$. The other input of both AND gates 78 and 80 is connected to a $f_0$ clock positive edge detection circuit (differentiator circuit) made up of capacitor C2 and resistor R2. The clock signal $f_0$ is applied to the R2-C2 circuit combination, which circuit differentiates the clock signal, causing positive pulses or spikes to be generated coincident with the positive-going transitions of the clock signal $f_0$, and negative-going pulses or spikes to be generated coincident with the negative-going transitions of the clock signal $f_0$. The negative-going transitions are not passed through the AND gates 78 and 80. However, the positive-going transitions are passed through the AND gates 78 and 80 when these gates are enabled. The result is that a positive strobe pulse, labeled STR in FIGS. 3A and 4, appears at the output of AND gate 78 coincident with the positive-going transitions of the clock $f_0$ when the AM demodulation signal exceeds $V_{Ref}$. Similarly, a positive strobe signal, labeled N-STR in FIGS. 3A and 4, appears at the output of AND gate 80 coincident with the positive-going transitions of the clock $f_0$ when the AM demodulation signal is less than $V_{Ref}$.

The strobe signal N-STR controls the operation of a switch S1. When the N-STR strobe pulse is present, S1 momentarily closes, connecting the capacitor C3 of the filter 58 to a reference potential, thereby dumping the charge on capacitor C3 at that time (positive-going edge of clock $f_0$) to an effective ground. In a like manner, the strobe signal STR controls the operation of another switch S2. When the STR strobe pulse is present, S2 momentarily closes, connecting the capacitor C3 to the input of integrator 62. This action transfers the charge on capacitor C3 at that time of the $f_0$ clock period (positive-going edge) to the integrator 62, where the charge value is integrated (summed with its prior value) and held until the next STR strobe pulse again causes switch S2 to close.

The integrator 62 comprises an operational amplifier 82 having a negative feedback loop made up of capacitor C4 in series with a resistor R4. As is well known in the electronic art, such a feedback loop, connecting the output of the amplifier through the feedback components to the negative input terminal, causes the amplifier 82 to integrate the value of the input signal, in this case electrical current (electrical charge per unit of time), applied to the negative input. The positive input of the operational amplifier 82 is coupled to a reference voltage, $+V_{DD}/2$. This reference voltage sets the operating point or bias point of the amplifier 82, both at its input terminals and output terminals, as well as the operating or bias point of the capacitor C3 of the filter 58. (That is, as shown in FIG. 3A, when switch S1 closes, the reference potential, or effective ground, to which the charge is dumped, is $+V_{DD}/2$.) Thus, as shown in the timing waveform diagram of FIG. 4, the signal "A" that is momentarily connected to the input of the integrator circuit 62 when switch S2 closes, is centered or biased about a voltage potential of $+V_{DD}/2$. This bias potential is selected because it is midway between ground (zero volts) and the maximum voltage potential available, $+V_{DD}$, thereby allowing maximum range for the signal "A" to vary in both directions.

The output signal from the integrator 62, labeled "B" in FIGS. 3A and 4 comprises a voltage level that assumes a value as determined by the amount of charge transferred to the input of the integrator 62 during the phase sample time, i.e., during that time when switch S2 is closed. The value of the "B" signal lies between zero volts and $+V_{DD}$, centered about $+V_{DD}/2$. That is, if at the phase sample time, the phase error is zero, the output signal "B" of the integrator 62 assumes a value of $+V_{DD}/2$. If, however, the phase error is not zero at the phase sample time, the output signal "B" assumes a value greater than or less than $+V_{DD}/2$ by an amount proportional to the phase error and in a direction (less than or greater than $+V_{DD}/2$) determined by the direction of the phase error. Advantageously, the operational amplifier 82 maintains this output voltage "B" at the indicated level until the next sample is presented to its input. Thus, for example, in FIG. 4, the integrator output "B" is shown as a voltage level that is just slightly above $+V_{DD}/2$ prior to the STR pulse 92. However, at the STR pulse 92, a phase error is detected, causing a "correction" to be made in the integrator output "B" signal. (It is noted that the vertical scale associated with the "B" signal of FIG. 4, wherein the correction as described above is illustrated, is greatly exaggerated relative to the vertical scales of the other signals shown in FIG. 4. This is done for emphasis and by way of example, and is not meant to represent a correction signal that may actually be required based on the other waveforms shown in FIG. 4, which other signals in fact do not depict a condition where a correction is needed.)

The output "B" from the integrator 64 is applied to a voltage-to-pulse width (PW) converter circuit 64, as shown in FIG. 3B. This converter circuit 64 functions as a pulse generator that produces a pulsed output signal, labeled "F" in FIGS. 3B and 4, having a duty cycle that varies as a function of the "B" signal voltage level. The converter circuit includes a comparator amplifier 84 having positive and negative input terminals. The "B" signal is applied to the positive terminal, and the $2f_0$ clock signal is applied to the negative terminal, as integrated by a low pass filter network comprising resistor R5 and capacitor C5. The values of resistor R5 and capacitor C5 are selected to be similar to the values R3 and C3, thereby causing a signal "E", appearing at the negative terminal of the comparator amplifier 84 to ramp in positive and negative directions. When the level of the input signal "B" exceeds the level of the ramped signal "E", the output signal "F" of the comparator amplifier 84 goes high. When the level of the input signal "B" is less than the level of the ramped signal "E", the output signal "F" goes low. The pulse width of the signal "F" thus varies at the level of the signal "B" changes. For example, if the signal "B" is approximately equal to $+V_{DD}/2$, a pulse width PW1 is obtained that is approximately ½ the duration of the period of the $2f_0$ clock, i.e., providing a 50% duty cycle. If the signal "B" is greater than $+V_{DD}/2$, as indicated by the dashed line in FIG. 4, then a pulse width PW2 is obtained that is measurably wider than the pulse width PW1, thereby providing a duty cycle that is greater than 50%. Similarly, although not shown in FIG. 4, if the signal "B" is less than $+V_{DD}/2$, then a pulse width is obtained that is less than PW1, thereby providing a duty cycle that is less than 50%.

The pulsed signal "F" is applied as a control signal to the binary controlled digital oscillator 66. The binary controlled digital oscillator 66 includes a crystal oscillator 86 that generates a high fixed frequency signal $f_c$. This high frequency signal $f_c$ is applied to the input of a random walk filter (RWF) 88. The pulsed signal "F" is also applied to the RWF 88 as a control signal. The RWF 88 is a divider circuit, dividing the input signal $f_c$ by $2-(1/k)$ when the control signal "F" is low, and by $2+(1/k)$ when the control signal "F" is high. The parameter k in this expression is a selectable parameter that sets the range within which the resulting output signal may vary. The output signal of the RWF 88 is a signal $f_w$ obtained by dividing the input signal $f_c$ as described. The signal $f_w$ serves as a source signal for the clock signal $f_0$. If the control signal "F" is a square wave having a 50% duty cycle, and having a period less than kT, where T is the period of the clock $f_0$, the division ratio remains fixed at 2. It takes k periods for the RWF 88 to adjust its output $f_w$ by one transition (add or delete one transition). The output of the RWF 88, $f_w$, is further divided in a counter circuit 90. This circuit divides the signal $f_w$ by n, where n is a selectable integer, to produce the clock signal $2f_0$, and by 2n, to produce the clock signal $f_0$.

As described, the pulse generator 64 thus transforms the integrator voltage "B" to a pulse-width modulation control signal "F" for the random walk filter 88. This configuration allows $f_0$ to be proportionally adjusted around the center frequency by any value of zero to plus or minus $f_0/2k$, proportional to the integrator output voltage "B". When the ASK input signal has zero amplitude, the integrator holds the last value, and the binary controlled oscillator coasts at the right frequency until the ASK amplitude is above the threshold $V_{Ref}$ and a new phase error sample is available.

In operation, the binary controlled digital oscillator 66 generates the clock signal $f_0$ and $2f_0$. The zero crossings of the ASK input signal, detected using the comparator circuit 54, are compared with the clock signal $2f_0$ in the digital phase detector 56. The output of the digital phase detector 56 comprises a digital signal that toggles between low and high values, having a high-to-low ratio that varies as a function of the phase difference between the carrier signal and the $2f_0$ clock. This digital phase difference signal is filtered (integrated) in filter circuit 58, thereby generating a phase error signal "A". At least once during each cycle of the $f_0$ clock, a determination is made as to whether the AM demodulation signal exceeds a prescribed threshold, $V_{Ref}$. If so, then it is presumed that the carrier signal is present within the ASK signal, rather than noise, and the positive strobe signal STR is generated. If not, then it is presumed that the carrier signal is not present within the ASK signal, and the negative strobe signal STR is generated. The positive strobe signal STR causes the phase error signal "A" to be transferred to the integrator circuit 62, where it is integrated (averaged) and held to produce an integrator output voltage level "B". The level of the signal "B" remains the same until the next positive strobe signal STR is generated, at which time this level may be adjusted or corrected as dictated by the sampled phase error at that time. The signal "B" is applied to the pulse generator 64, causing the pulse width of the resulting pulse output signal "F" to change proportional to the level of the signal "B". In turn, the pulse signal "F" controls the random walk filter 88 of the binary controlled oscillator, thereby causing the phase (instantaneous frequency) of the clock signals $2f_0$ and $f_0$ to move in a direction that minimizes the phase error. In this manner, the clock signal $f_0$ is phase-locked to the carrier signal appearing in the ASK signal during those times when the carrier signal is present. During those times when the carrier signal is not present, the clock signal $f_0$ coasts at a frequency and phase that was phase-locked to the carrier signal of the ASK signal when the carrier signal was last present in the ASK signal.

In the preferred embodiment, the threshold $V_{Ref}$ of the sample enable circuit 60 is selected to be 0.75 $V_p$, where $V_p$ is the peak voltage of the AM demodulated signal. The logic circuits described above (AND gates, exclusive OR gates, flip flops, invertors, counters, etc.) may be realized using any suitable logic family of integrated circuits, such as the relatively inexpensive 54L/74L series, or the CMOS 4000 series. The comparator amplifiers and operational amplifiers may likewise be realized using commercially available comparator amplifiers, such as the LM311 comparator amplifier, or the TLC27M2 operational amplifier. The switches S1 and S2 may also be realized using commercially available components, such as the CMOS switch CD4053. The random walk filter 88 is preferably a 54LS/74LS297 Digital Phase-Locked Loop Filter, available from Texas Instruments. The crystal oscillator 86 operates at a frequency of 2.097 MHz. The value of k for the random walk filter is selected to provide a range of ±16 Hz in the clock signal $f_0$. The preferred frequency of the clock $f_0$ is 8192 Hz. Hence, assuming that the random walk filter divides the crystal oscillator frequency by 2, on average, making $f_w$ approximately equal to 1.0485 MHz, the value of n is selected to be 64. This makes the clock signal $2f_0$ ($f_w/n$) equal to 16,384 Hz, and makes the value of the clock signal $f_0$ ($f_w/2n$) equal to the desired 8192 Hz.

As described above, it is thus seen that the present invention provides a sample-and-hold digital phase-locked loop (PLL) circuit that samples the phase error between an input signal and a clock signal (the PLL's output signal) only when the energy level of the input signal, such as is measured by AM demodulating the input signal, exceeds a prescribed threshold level. It is also seen that the present invention provides such a digital PLL wherein the sampled value of the phase error is held until the next sample is taken at a time when the energy level of the carrier signal exceeds the threshold, thereby assuring that the clock signal of the PLL does not attempt to lock on low level input signals, but rather coasts at the right frequency until a new phase error sample is available. It is further seen that the present invention provides a digital PLL wherein the frequency, and thereby the phase, of the clock signal can be adjusted to any value within a range of $f_0 \pm f_0/k$ Hz (where $f_0$ is the center frequency of the clock signal, and k is a selectable parameter), not just to discrete values within such range, as is common in prior art digital PLL's. Finally, it is seen that the present invention provides a PLL that is inexpensive to fabricate, simple to operate, and yet provides accurate performance, thereby making the PLL ideally suited for use in telemetry channels of the implantable device art.

While the invention herein disclosed has been described by means of specific embodiments and applications thereof, numerous modifications and variations could be made thereto by those skilled in the art without departing from the scope of the invention set forth in the appended claims.

I claim:

1. In a communication channel between an implanted device and a non-implanted device wherein an amplitude shift keyed (ASK) data signal is generated in one and received in the other of said implanted and non-implanted devices, a first binary state being indicated within said generated ASK data signal by the presence of a carrier signal, and a second binary state being indicated within said generated ASK data signal by the absence of said carrier signal, said generated ASK data signal comprising a data stream of binary bits, where each binary bit comprises a prescribed number of periods of said carrier signal during which said generated ASK data signal assumes either said first or second binary state, demodulation apparatus for demodulating said received ASK data signal comprising:
    means for generating a clock signal that is phase-locked with the carrier signal of said received ASK data signal when said carrier signal is present within said received ASK data signal, and that is phase-locked to the carrier signal that was most recently present within said received ASK data signal when said carrier signal is absent from said received ASK data signal; and
    decision means synchronized with said clock signal for: (1) determining whether said received ASK data signal indicates a first binary state, and if so for how many periods of said clock signal said first binary state continues, and (2) determining whether said received ASK data signal indicates a second binary sate, and if so for how many periods of said clock signal said second binary state continues;
    whereby said data stream of binary bits within said generated ASK data signal can be recreated from said received ASK data signal by said demodulation apparatus.

2. The demodulation apparatus as set forth in claim 1 wherein said clock signal generating means comprises:
    means for generating a local clock signal that has a frequency approximately equal to the frequency of said carrier signal within said received ASK data signal, the frequency of said local clock signal being adjustable as controlled by a control signal;
    means for measuring a phase error between said local clock signal and said carrier signal;
    sampling means for sampling the phase error between said carrier signal and said local clock signal at least once curing each period of said carrier signal only when said carrier signal is present within said received ASK data signal;
    integrating means for integrating the most recent sampled phase error obtained from said sampling means and for holding the resulting integrated sampled phase error until said sampling means again samples the phase error between said carrier signal and said clock signal, an output signal of said integrating means thereby comprising the integral of the most recent sampled phase error presented to the input of said integrating means;
    means responsive to said output signal of said integrating means for generating said control signal, said control signal being applied to said local clock signal generation means to adjust the frequency thereof in a direction that minimizes the phase error between said local clock signal and said carrier signal;
    whereby said local clock signal assumes a frequency that is phase-locked to the carrier signal included within said received ASK data signal when said carrier signal is present within said received ASK data signal, and that assumes a frequency that is phase-locked to the carrier signal that was most recently present within said received ASK data signal when said carrier signal is absent from said received ASK data signal.

3. Demodulation apparatus as set forth in claim 2 wherein said sampling means includes detection means for determining an average amplitude of the carrier signal within said received ASK data signal, and for detecting when the average amplitude of said carrier signal exceeds a prescribed threshold level.

4. Demodulation apparatus as set forth in claim 2 wherein said local clock signal generating means comprises a binary controlled digital oscillator, said binary controlled digital oscillator providing said local clock signal as an output signal, the frequency of said local clock signal being controllable by a binary control signal having one of two levels, the local clock signal increasing in frequency in response to one level of said binary control signal and decreasing in frequency in response to the other level of said binary control signal; and further wherein said control signal generating means generates said binary control signal to assume one of said first or second levels depending upon whether the frequency of said local clock signal should increase or decrease in order to minimize the phase error between said clock signal and said carrier signal.

5. Demodulation apparatus as set forth in claim 4 wherein said control signal generating means causes said binary control signal to assume a duty cycle that is substantially equal to 50% when the phase error between the carrier signal and the local clock signal is substantially zero, and to assume a duty cycle greater than 50% when the phase error is of one polarity, and to assume a duty cycle less than 50% when the phase error is of the opposite polarity.

6. Demodulation apparatus as set forth in claim 5 wherein the output signal of said integrating means comprises an analog voltage that may assume any value between a range of maximum and minimum values, and wherein said control signal generating means comprises a voltage-to-pulse width converter circuit providing an output pulsed signal having a duty cycle that is proportional to the value of said analog voltage.

7. Apparatus for generating a clock signal that is phase-locked with an amplitude modulated (AM) carrier signal, and apparatus comprising:
 means for generating a lock clock signal that has a frequency approximately equal to the frequency of said carrier signal, the frequency of said local clock signal being adjustable as controlled by a control signal;
 phase detector means for detecting the phase error between said carrier signal and said local clock signal;
 means for determining an average amplitude of said AM carrier signal and comparing said average amplitude to a prescribed value;
 sampling means for sampling the phase error detected by said phase detector means at least once during each period of said carrier signal only when the average amplitude of said AM carrier signal exceeds said prescribed value, whereby the phase error is not sampled when the average amplitude of said AM carrier signal is less than said prescribed value;
 integrating means for integrating the most recent sampled phase error obtained from said sampling means and for holding the resulting integrated sampled phase error until said sampling means again samples the phase error between said input signal and said clock signal, and output signal of said integrating means thereby comprising the integral of the most recent sampled phase error presented to the input of said integrating means; and
 means responsive to said output signal of said integrating means for generating said control signal, said control signal being applied to said local clock signal generation means to adjust the frequency thereof in a direction that minimizes the phase error between said local clock signal and said AM carrier signal.

8. Apparatus as set forth in claim 7 wherein said AM carrier signal is modulated with digital data, said AM carrier signal assuming one of two possible amplitudes, a first amplitude representing one state of said digital data, and a second amplitude representing another state of said digital data, and further wherein said prescribed value associated with said sampling means lies between said first and second amplitudes, whereby said phase error is sampled if the digital data modulating said AM carrier signal is of one state, and the phase error is not sampled if the digital data modulating the AM carrier signal is of the other state.

9. Apparatus as set forth in claim 8 wherein said first amplitude of said digital AM carrier signal comprises zero and said second amplitude comprises a peak amplitude value, whereby said digital AM carrier signal comprises an amplitude shift keyed (ASK) signal wherein the presence of said carrier signal at said peak amplitude value indicates one state of said digital data, and the absence of said carrier signal indicates the other state of said digital data, said prescribed value associated with said sampling means comprising a value that is greater than 50% of said peak amplitude value.

10. Apparatus as set forth in claim 9 wherein said prescribed value associated with said sampling means comprises a value that is at least 70% of said peak amplitude value.

11. Apparatus as set forth in claim 7 wherein said sampling means comprises
 means for generating an AM demodulated signal that assumes a value that substantially follows the peak values of the AM carrier signal;
 threshold means for comparing said AM demodulated signal to said prescribed value and for generating an enabling pulsed signal at least once during each period of said local clock signal when said AM demodulated signal exceeds said prescribed value; and
 switch means responsive to said enabling pulsed signal for momentarily connecting the output of said phase detector means to said integrating means.

12. Apparatus as set forth in claim 11 wherein said threshold means also generates a disabling pulsed signal at least once during each period of said local clock signal when said AM demodulated signal is less than said prescribed value, and further wherein said switch means momentarily connects the output of said phase detector means to a ground potential in response to said disabling pulsed signal.

13. Apparatus as set forth in claim 11 wherein said phase detector means comprises:
 a flip flop circuit that changes to a first state in synchrony with each transition of said local clock signal, and that is reset to a second state in synchrony with each zero crossing of said AM carrier signal, said first and second states being manifest by a flip flop output voltage that alternates between a low level and a high level; and
 an integrating filter coupled to the output of said flip flop circuit, said integrating filter including a first capacitor that stores an electrical charge associated with the output voltage levels assumed by said flip flop circuit, said electrical charge ramping to a positive peak value in response to a change in the flip flop output voltage from a low level to a high level, and ramping to a negative peak value in response to a change in the flip flop output voltage from a high level to a low level.

14. Apparatus as set forth in claim 13 wherein said switch means transfers the charge on said first capacitor at the time of said enabling pulsed signal to an input of said integrating means.

15. Apparatus as set forth in claim 7 wherein said means for generating said local clock signal comprises a binary controlled digital oscillator, said binary controlled digital oscillator providing said local clock signal as an output signal, the frequency of said local clock signal being controllable by a binary control signal having one of two levels, the local clock signal increasing in frequency in response to one level of said binary control signal and decreasing in frequency in response to the other level of said binary control signal; and further wherein said control signal generating means generates said binary control signal to assume one of said first or second levels depending upon whether the frequency of said local clock signal should increase or decrease in order to minimize the phase error between said clock signal and said carrier signal.

16. Apparatus as set forth in claim 15 wherein said control signal generating means causes said binary control signal to assume a duty cycle that is substantially equal to 50% when the phase error between the carrier signal and the local clock signal is substantially zero, and to assume a duty cycle greater than 50% when the phase error is of one polarity, and to assume a duty cycle less than 50% when the phase error is of the opposite polarity.

17. Apparatus as set forth in claim 16 wherein the output signal of said integrating means comprises an analog voltage that may assume any value between a range of maximum and minimum values, and wherein said control signal generating means comprises a voltage-to-pulse width converter circuit, said voltage-to-pulse width converter circuit providing an output pulsed signal having a duty cycle that is proportional to the value of said analog voltage.

18. Apparatus as set forth in claim 17 wherein said binary controlled digital oscillator comprises:
a reference oscillator that produces a continuous reference signal having a fixed frequency f1;
a random walk filter that divides said reference signal by an amount 2+(1/k) whenever said output pulsed signal from said voltage-to-pulse width converter circuit assumes one level, and by an amount 2−(1/k) whenever said output pulsed signal assumes another level, where k is a selectable division factor; and
a counter circuit that divides the output signal from said random walk filter by an integral number in order to produce said local clock signal.

19. Apparatus as set forth in claim 18 wherein said fixed frequency f1 of said reference oscillator comprises 2.097 MHz; and the frequency of said local clock signal and said carrier signal comprises 8192 kHz.

20. A sample-and-hold digital phase-locked circuit for providing a local clock signal that is phase-locked to a carrier signal included within an amplitude shift keying (ASK) input signal, comprising:
binary controlled digital oscillator means for generating said local clock signal;
pulse generator means for generating a binary signal that controls said binary controlled digital oscillator as a function of a first input signal;
phase detector means for measuring the phase error between said local clock signal and said input ASK signal;
threshold means for determining an average amplitude of the carrier signal within said ASK input signal and comparing said average amplitude to a prescribed threshold;
sampling means for sampling the phase error measured by said phase detector means at least once during each cycle of said local clock signal when the average amplitude of said carrier signal exceeds said prescribed threshold; and
integrator means for integrating said sampled phase error from said sampling means, said integrated sampled phase error obtained from said integrator means comprising said first input signal applied to said pulse generator, said first input signal being applied to said pulse generator until said sampling means provides a new sample of the phase error to said integrator means.

21. A method for extracting a clock signal that is phase-locked with an input signal modulated by amplitude shift keying (ASK) comprising the steps of:
(a) generating a local clock signal having a frequency that varies as a function of a control signal;
(b) detecting the phase difference between the ASK input signal and the local clock signal;
(c) generating an error signal as a function of the phase difference detected in step (b);
(d) comparing the amplitude of the ASK input signal with a prescribed threshold value;
(e) sampling said error signal only when the amplitude of the ASK input signal exceeds said prescribed threshold value;
(f) integrating said sampled error signal;
(g) generating said control signal as a function of the integrated sampled error signal as a step (f) and maintaining the value of said control signal at a substantially constant value until the error signal is again sampled; and (h) adjusting the frequency of said local clock signal as a function of the value of said control signal.

22. The method as set forth in claim 21 wherein step (g) further includes converting said constant value control signal to a pulsed signal having a duty cycle that varies as a function of said control signal, and step (h) includes adjusting the frequency of said local signal as a function of the duty cycle of said pulsed signal.

23. The method as set forth in claim 22 wherein step (a) includes generating a stable reference signal, dividing said stable reference signal by an amount 2+(1/k) when said pulsed signal assumes a first value, and by an amount 2−(1/kz) when said control signal assumes a second value, where k is a programmable integer, the output signal resulting from said division comprising a source signal for said local clock signal.

24. The method as set forth in claim 21 wherein step (e) comprises generating an AM demodulated signal from said ASK input signal, applying said AM demodulated signal to a threshold detector, generating a first strobe signal once each cycle of said local clock signal only when said AM demodulated signal exceeds said prescribed threshold as determined by said threshold detector, and using said first strobe signal to sample said error signal.

25. The method as set forth in claim 24 wherein the step of using said strobe signal to sample said error signal comprises applying said strobe signal to a switch circuit that switchably connects said error signal to an integrator circuit for the duration of said first strobe signal.

26. The method as set forth in claim 24 further including generating a second strobe signal once each cycle of said local clock signal when said AM demodulated signal is less that said prescribed threshold as determined by said threshold detector, and using said second strobe signal to connect said error signal to ground for the duration of said second strobe signal.

* * * * *